(12) United States Patent
Chaswal et al.

(10) Patent No.: US 8,409,071 B2
(45) Date of Patent: Apr. 2, 2013

(54) METHOD AND APPARATUS FOR TREATMENT PLANNING USING IMPLANTED RADIOACTIVE SOURCES

(75) Inventors: Vibha Chaswal, Madison, WI (US); Bruce R. Thomadsen, Madison, WI (US); Douglass L. Henderson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1041 days.

(21) Appl. No.: 12/413,256

(22) Filed: Mar. 27, 2009

(65) Prior Publication Data

US 2009/0182187 A1    Jul. 16, 2009

Related U.S. Application Data

(63) Continuation-in-part of application No. 11/130,967, filed on May 17, 2005, now Pat. No. 7,762,940.

(60) Provisional application No. 61/042,136, filed on Apr. 3, 2008.

(51) Int. Cl.
*A61M 36/04* (2006.01)

(52) U.S. Cl. .......................................................... 600/3

(58) Field of Classification Search ................. 600/1–8; 205/493.1–504 H; 424/1.11–1.89; *A61M 36/14*
See application file for complete search history.

(56) References Cited

U.S. PATENT DOCUMENTS

| | | | |
|---|---|---|---|
| 6,327,490 B1 | 12/2001 | Spetz | |
| 6,387,034 B1 | 5/2002 | Lee | |
| 6,512,942 B1 | 1/2003 | Burdette et al. | |
| 6,530,873 B1 | 3/2003 | Lee | |
| 6,539,247 B2 | 3/2003 | Spetz | |
| 2002/0177748 A1 | 11/2002 | Munro, III | |
| 2003/0130573 A1 | 7/2003 | Yu et al. | |
| 2003/0233123 A1* | 12/2003 | Kindlein et al. | 607/2 |
| 2004/0092786 A1 | 5/2004 | Zaider et al. | |
| 2004/0225174 A1 | 11/2004 | Fuller et al. | |
| 2008/0242914 A1* | 10/2008 | Henderson et al. | 600/1 |

* cited by examiner

*Primary Examiner* — Charles A Marmor, II
*Assistant Examiner* — Catherine E Burk
(74) *Attorney, Agent, or Firm* — Boyle Fredrickson, S.C.

(57) ABSTRACT

A pre-computed importance function providing ex ante assessment of optimal placement of a single radioactive source is used for sequential placement of multiple radioactive sources. As each source is placed, the importance function may be modified to reflect the dose implemented by that source and all sources already placed. The greedy algorithm employed by this technique makes possible optimization of additional dimensions of treatment planning including, using directional and isotropic sources, using different source isotopes, using optimum source strengths, using source locations that are not on the regular grid and using a single movable source for variable times at different locations.

21 Claims, 9 Drawing Sheets

METHOD AND APPARATUS FOR TREATMENT PLANNING USING IMPLANTED RADIOACTIVE SOURCES

CROSS-REFERENCE TO RELATED APPLICATIONS

This application claims the benefit of U.S. Provisional application 61/042,136 filed Apr. 3, 2008 hereby incorporated by reference and is further a continuation-in-part of U.S. application Ser. No. 11/130,967, filed on May 17, 2005 now U.S. Pat. No. 7,762,940, entitled: Directionally Emitting Radioactive Sources for Brachytherapy, all hereby incorporated by reference.

STATEMENT REGARDING FEDERALLY SPONSORED RESEARCH OR DEVELOPMENT

-

BACKGROUND OF THE INVENTION

The present invention relates to radiation therapy for the treatment of cancer and the like and, in particular, to a planning method and to an apparatus for radiation therapy using implanted radioactive sources.

Prostate implant brachytherapy is a radiation treatment technique in which radioactive sources are implanted directly into the prostate and either moved or removed after a period of time or left in place permanently. For permanent brachytherapy, typically 44 to 100 small radioactive sources are implanted near the tumorous tissue. Temporary brachytherapy is where sources are inserted into or near tissue to be treated, left in place for hours or days, and then removed. High dose-rate implants refer to a special case of temporary implants where the catheters are implanted in the treatment target and a single movable high dose-rate source is made to dwell (for times ranging between 0.1 s to a few minutes) at various locations in the tumorous tissue, delivering the dose in less than one hour. While treatment of prostate cancer is used as an example, nothing about this invention limits it use to that body site or disease.

The sources may be a radioactive material adsorbed onto small resin spheres or other carriers contained within a titanium capsule or on the surface of a silver rod also sealed in titanium. Depending on the radionuclide used, the sources typically have a half-life of approximately 3 to 180 days, but not limited to that range, providing an average energy of emitted photons of approximately, but not limited to 20 to 600 keV with a typical commercial source strength in the range of 0.1-5 mCi for permanent implants and approximately 10 Ci for high dose-rate sources, although other strengths may be used. Example radionuclides used are 125I, 103Pd or 131Cs for permanent brachytherapy and 192Ir for high dose rate brachytherapy, or 192Ir or 125I for temporary low dose-rate applications. Other radionuclides may also be used. The sources may be generally isotropic, having uniform radiation patterns (e.g. radially symmetric about the source), or may be anisotropic or directional, for example by incorporating small shields into the source that focus the radiation pattern in one direction.

In permanent low dose rate brachytherapy, the sources are of a size, e.g., 0.8 mm in diameter and 4.5 to 5 mm long, so that they may be implanted using a hollow needle. The needle provides a lumen 1.3 to 1.5 millimeters in diameter and about twenty centimeters long into which sources may be inserted along with spacers controlling their separation. The loaded needle is inserted into the patient and then withdrawn while a plunger ejects the contained sources.

Placement of the sources, for example, for use in treatment of the prostate may be done transperineally and the needles are guided by a plate having predrilled holes on a regular grid. The depth of insertion of the needles is normally guided by an image obtained with a transrectal ultrasonic imaging device. In this way, sources may be accurately placed at selected regular grid locations.

In temporary implants using high dose rate brachytherapy, a small source with dimensions 0.7 mm diameter and 3-4 mm in length is welded to the tip of a flexible stainless steel cable, which travels in and out of the hollow catheters with dwell positions at every 5 mm interval. A source moves in steps through the catheters, stopping at selected dwell positions for a pre-calculated amount of time to deliver the required radiation dose.

The locations of the radioactive sources along the grid or dwell locations and corresponding dwell time along the catheters are desirably selected to provide the prescribed dose to the diseased tissue of the prostate while sparing surrounding sensitive critical tissue, for example, the urethra and rectum. Such selection/placement is aided by treatment planning performed before the implantation of the sources.

In current practice, treatment planning is largely trial and error based on some simple spacing rules after an inspection of the tumor site by ultrasonic or other imaging techniques. More precise treatment planning may be obtained by a number of well known optimization processes providing mathematical simulation of a dose from a given source pattern.

Determining the dose produced by "forward" calculations, i.e., from a given pattern of sources is a relatively straightforward process, however, the "backwards" calculation from the desired dose to a source pattern is mathematically difficult. Such problems are typically addressed by stochastic techniques, such as "simulated annealing" or by "genetic algorithms" that perform repeated forward calculations for many possible source patterns and then apply an objective function to dose produced by the pattern to select the best pattern.

A deterministic approach to treatment planning is provided by the "branch and bound" method described, for example, in "Treatment Planning for Brachytherapy: An Integer Programming Model, Two Computational Approaches and Experiments With Permanent Prostate Implant Planning", by Lee E. K. et al., Phys. Med. Biol. 44: 145-165 (1999), and "An Iterative Sequential Mixed-Integer Approach to Automated Prostate Brachytherapy Treatment Plan Optimization", D'Souza W. D. et al., Phys. Med. Biol. 46: 297-322 (2001).

Operating on high-speed computers, these approaches may take minutes to more than half an hour to complete for a typical prostate treatment plan and may also involve varying degrees of manual intervention. Such delay imposes considerable inconvenience and expense on a patient, either in waiting for the implant during the treatment planning process, or in having to return after the treatment planning session at a later date for the implanting or in paying for the Operation Room time involved in the procedure. Manual intervention makes treatment planning a subjective task and reproducibility of the same quality implants becomes a matter of concern. In addition, the time involved in such feedback oriented and trial and error based optimization techniques make the treatment planning inappropriate for application into intraoperative or interactive brachytherapy where the treatment plan needs to be generated inside the operation theater with the patient in treatment position. With patient under anesthesia, every minute added to the delay in treatment planning counts.

Availability of a fast as well as reliable treatment planning technique therefore, holds utmost importance.

The parent application to the present application describes an improved treatment planning technique in which an "importance function" is precomputed and then used without modification to locate sources in a sequential process in which the sources are not repositioned after they are located. An exclusion zone is placed around each source to prevent this sequential placement from producing clusters of sources in the high importance areas at the expense of other portions of the tumor. By using a "greedy" algorithm, processing time is substantially decreased.

A greedy algorithm is any algorithm that follows the strategy of making a locally optimum choice at each stage with the hope of finding the global optimum. The greedy heuristic method for treatment planning optimization is fundamentally different from other dynamic optimization methods, such as simulated annealing, genetic algorithm and branch and bound method. The choice made by a greedy algorithm may depend on choices already made but not on future choices or of the solutions to the sub-problem. It sequentially makes one greedy choice after another, reducing each given problem into a smaller one. In other words, a greedy algorithm never reconsiders its choices.

This is the main difference from dynamic programming. After every stage, dynamic programming makes decisions based on all the decisions made in the previous stage, and may reconsider the previous stage's algorithmic path to solution.

Another difference between the dynamic programming and the greedy is that dynamic programming is exhaustive and is often guaranteed to find the optimum solution, whereas the greedy provides a good, near optimum solution for must problems and the optimum for a few problems.

SUMMARY OF THE INVENTION

The present invention provides an improvement on the algorithm of the parent process, which retains the "greedy" quality of the previous technique (that is, sources are not moved once they are placed) but eliminates the arbitrary exclusion zones in favor of a time-efficient calculation determining the effect of the placed source(s). Improvements in both speed and accuracy are thereby obtained.

The present invention is applicable to treatment planning using directional sources, mixtures of directional sources and isotropic sources, and sources of different species, for permanent or temporary low dose rate brachytherapy implants. For high dose rate implants, the present invention is capable of generating dwell-time distributions. The improved processing speed of the present technique permits these more complex planning scenarios. It also is applicable to implants performed without limiting templates, such as those using robotic delivery or a free-hand implantation. And it is also capable of techniques where the treatment planning algorithm generates the optimum source strength to be used in an implant in addition to the source locations.

Specifically the present invention provides a method of treatment planning for placement of radioactive sources in a tumor in a region of a body. In a first step, the individual dose patterns for a range of locations within the tumor region of the body is determined. Next, an importance function is developed for the range of locations based upon the volume distribution of the dose pattern produced by a hypothetical source moved among the range of locations. Using the locations according to the importance function, a ranking of locations is made. Then, based on the ranking, a source location not currently reserved for a source is identified and reserved. Based on the dose from this new reserved source, an evaluation function is created being a combination of the importance function and the total dose provided by sources at reserved locations. A new ranking is assigned to all locations based on the evaluation function. Then, based on the rankings, the next source location is identified. This process is repeated using the evaluation function to perform the ranking until the prescribed dose is obtained to within a predetermined matching criterion. A treatment plan is then provided for treating a patient by irradiating the tissue with at least one radioactive source located at each of the reserved locations.

It is thus one feature of the invention to provide the performance speed of a greedy algorithm while improving the accuracy of source placement by taking into account the dose produced by previously selected source locations so that a real-time dose accounting may be performed while the treatment planning is done.

The placement of sources may not be limited to template grid defined locations and sources may be placed at locations that are off the grid for better coverage of the tumorous tissue.

It is further a feature of the invention to provide optimized locations for source positions not limited to template-constrained positions.

The calculation of the evaluation function may scale values of the importance function by a function related to ratio of the cumulative dose provided by sources at currently reserved locations and the prescribed dose.

It is thus another feature of the invention to provide a method of calculating a ranking based on evaluation function that can be done repeatedly without undue computational burden. By scaling a pre-existing importance function by a function related to the cumulative dose so far, a new evaluation function may be rapidly generated as sources are placed.

The treatment plan may either describe a positioning of sources permanently implanted at each of the reserved locations or a dwell time distribution for the movement of a radioactive source placed temporarily at the reserved locations.

It is thus a feature of the invention to provide a radiation treatment planning system adaptable to a wide variety of radiation therapy approaches, temporary or permanent implants.

The importance function may evaluate the amount of dose to the tumor treated versus the amount of dose to non-tumor tissue. For example, the importance function may be a ratio, the numerator of which is weighted dose to non-tumor tissue and the denominator of which is weighted dose to tumor tissue, or other function such as a difference of these doses.

It is thus a feature of the invention to provide a mathematically simple importance function that can guide a greedy algorithm ex ante.

The importance function may incorporate a consideration of the homogeneity of the dose in the tissue being treated. It may also evaluate real-time effect of placement of a source on the overall dose homogeneity of an implant. For example, the evaluation function may be a product of pre-computed effect on dose-homogeneity from a single hypothetical source and cumulative dose homogeneity from all the placed sources at reserved locations.

It is thus a feature of the invention to allow tailoring of the importance function to promote the goal of homogeneity.

It is of importance to keep the number of needles low in an implant. The ranking may order source locations according to the evaluation function as modified by a needle function. The needle function may accept as an argument the maximum number of needles that may be user-specified, and the current number of needles necessary to locate sources at currently reserved locations. The needle function decreasing the weight of the importance function for the given location in the ranking as the number of needles increases.

It is thus a feature of the invention to use a calculational framework to promote the goal of limiting the number of needles.

The optimization process described may also proceed in a manner to determine the optimal strength of sources (these are strengths other than commercially available strengths) to yield an implant with high uniformity, conformality or other characteristic evaluated by the user.

It is thus a feature of the invention to incorporate an evaluation characteristic in the calculational frame-work to determine optimal strength of sources in a treatment plan.

The importance or evaluation function may consider a hypothetical directional source at different rotated orientations and the ranking adopts the rotation having the best value of the importance function for the directional source.

It is thus a feature of the invention to readily incorporate the use of directional sources into the treatment plan.

The importance or evaluation function may consider both hypothetical directional sources and hypothetical isotropic sources and the ranking adopts an isotropic source when a variance of importance function values for a directional source at the same location for different rotations is below a predetermined threshold. Alternatively, the importance or evaluation function may consider both hypothetical directional sources and hypothetical isotropic sources, and the importance or evaluation function provides weighting to the non-tumor tissue dose so that most sources selected in the ranking are isotropic.

It is thus a feature of the invention to provide a radiation treatment planning system that does not over-emphasize the use of directional sources.

The importance or evaluation function may consider different species of hypothetical sources and the ranking may adopt the species having the best value of importance function for a given location.

It is thus another feature of the invention to provide a treatment planning system readily adaptable to treatment plans having mixed source types or radioactive species.

The importance or evaluation function may consider repetitive selection of a location as required for differential loading when only one source dwells at various locations for variable amounts of time in temporary implants.

It is thus another feature of the invention to provide a treatment planning system readily adaptable to treatment plans for high dose rate brachytherapy.

These particular features and advantages may apply to only some embodiments falling within the claims and thus do not define the scope of the invention.

DETAILED DESCRIPTION OF THE PREFERRED EMBODIMENT

Brachytherapy Apparatus

Figure 1:
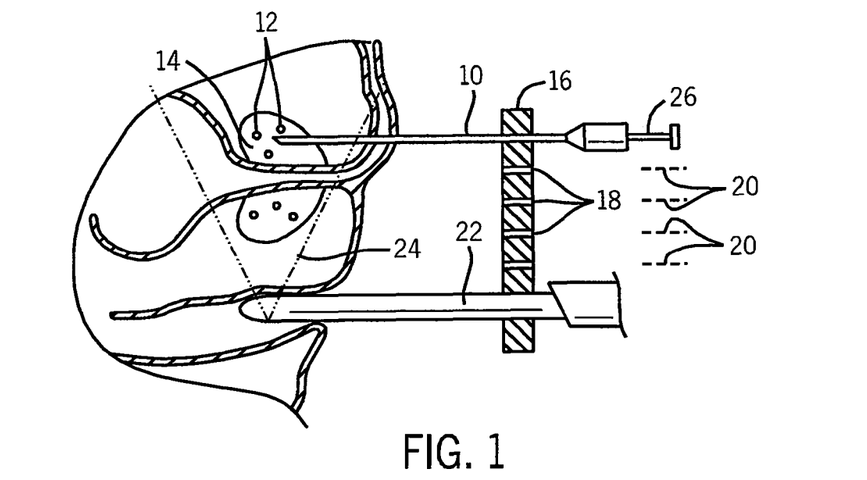
FIG. 1 is a fragmentary, cross-sectional view taken along a mid-sagittal plane of a patient receiving radioactive sources for treatment of the prostate, such as may be guided by the present invention.

Referring now to FIG. 1, prostate brachytherapy may employ a hollow needle 10 to place radioactive sources 12 within the prostate 14 transperineally. The needle 10 is guided by a plate 16 having a plurality of guide holes 18 placed at regular grid locations 20 over two dimensions of the plate 16. The plate may be clamped to a trans-rectal ultrasonic probe 22 providing an ultrasonic beam 24 illuminating the prostate 14 so as to verify the depth of placement of the sources 12 as they are ejected from the needle 10 by means of a plunger 26 fitting within the hollow shaft of the needle 10. The sources 12 may be placed within the needle 10 in a preconfigured separation enforced by nonradioactive spacers.

Alternatively, the needle 10 may be positioned without the plate 16 by means of a robotic positioner. And in yet a further embodiment, the needle 10 may support a movable radioactive source, for example at the tip of the plunger 26, that may be moved along the needle 10 to different locations to provide a dose at those locations determined by the dwell time of the source at the location. In this case the source may be a radioactive isotope or may, for example, be a miniaturized electronic x-ray source or the like.

Figure 2:
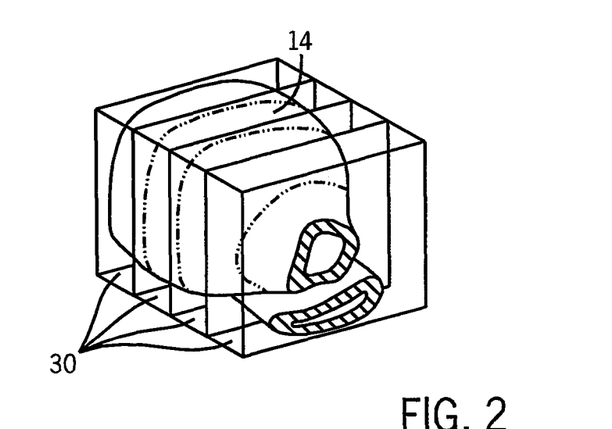
FIG. 2 is a perspective view of the prostate of FIG. 1 as divided into a series of slices that may be imaged with a trans-rectal probe to guide the placement of sources.

The present invention provides a treatment planning system for prostate brachytherapy that determines where sources 12 should be placed. Referring to FIG. 2, prior to the treatment planning, a region of interest generally including both the prostate 14 and tissue around the prostate is preferably imaged. The images, for example, may be composed of a series of slices 30 obtained trans-rectally by the trans-rectal ultrasonic probe 22 as B-mode images. The slices 30 may be viewed individually on a screen of the ultrasound machine (not shown) or on a separate computer, either of which may be programmed to perform or assist in performing the treatment planning itself.

Figure 3:
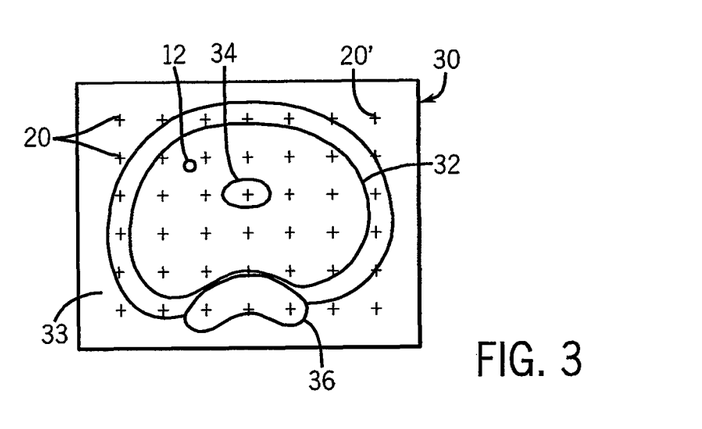
FIG. 3 is a view of one plane of FIG. 2 in which the prostate, urethra, and rectum have been outlined by a physician to show treatment regions, and further showing a grid of possible source locations.
Figure 4:
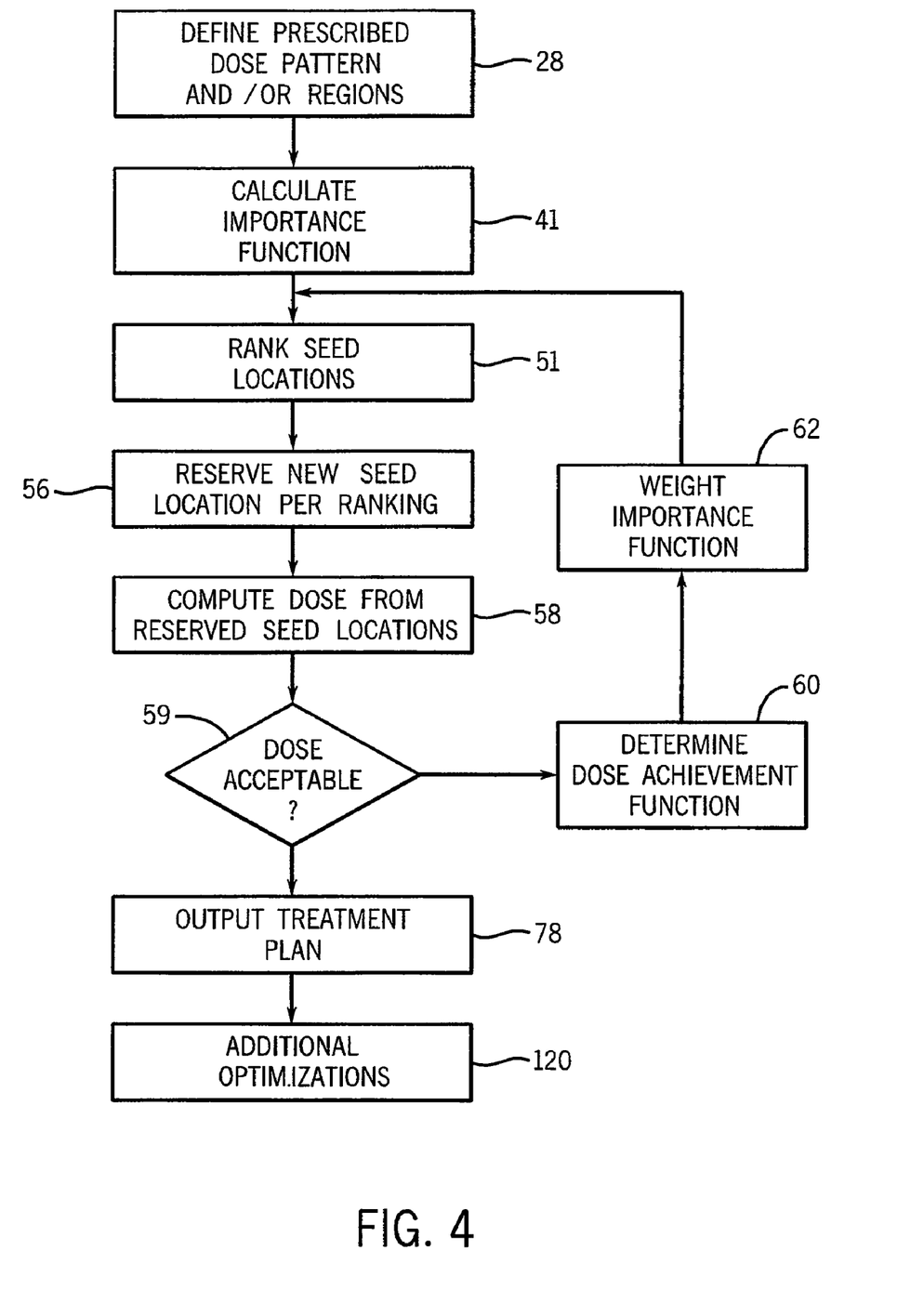
FIG. 4 is a flowchart of the method of the present invention as may be implemented in whole or in part in the software.

Referring to FIGS. 3 and 4, in a first step of the treatment planning indicated by process block 28, each slice 30 may be viewed by a physician and used to identify different regions requiring different doses. In the case of the prostate, the prostate region 32, for example, may be outlined by the physician using a cursor or similar device on a displaying ultrasound machine or terminal (not shown). Centered within the prostate region 32 is the urethral region 34, and posterior to the prostate region 32 is the rectal region 36 which may also be outlined and identified as such by the physician. The remaining tissue in this vicinity is considered normal tissue 33. Each of these regions has a volume in three dimensions as may be constructed on a slice-by-slice basis with each slice outlined by the physician. As shown in FIG. 3, grid locations 20 are input to the computer corresponding to locations defined by the plate 16 and depths along a needle held by the plate at a location and optionally displayed. Or, as will be described below in an alternative embodiment, a range of grid location spacings, corresponding to different plates 16 or a continuously movable robotic manipulator, may be entered with the program to select the optimum source 12 location spacing. Other treatment planning parameters may be entered at this time including the prescribed dose, the types of sources, directional and isotropic sources, as well as definitions of various functions and their parameters such as those defining the ex-ante importance function, the evaluation function, needle penalty function etc as will be described below, all of which may be modified by the user.

Generating an Ex Ante Importance Function

Referring again to FIG. 4, once the regions have been identified and the sample parameters input per process block 28, the program pre-calculates for each region an importance function, also termed an "adjoint function", based on the particular sources 12, the defined prostate region 32, the urethral region 34, and the rectal region 36 as indicated by process block 41. Again, while the example is of a prostate implant, this approach is not limited to any anatomical site or type of target tumor. A different adjoint function is established for each of the regions 32, 34, and 36 and is determined by computing the average dose value that would be received by the regions 32, 34, and 36 from a radioactive source placed at each different grid location 20 within the areas of the image of the slice 30. The average dose value can be computed using a forward transport calculation, or similar techniques, such as are well known in the art. Thus, for grid location 20' in the upper left-hand corner of the image of the slice 30, the height of the distribution sensitivity for the rectal region 36 would be the average dose received by all the points within the rectal region 36 from a source 12 at grid location 20'.

The calculation of dose used to compute the adjoint functions may employ a number of well-known forward dose modeling techniques and, in the preferred embodiment, assumes a standard tissue characteristic for each of the regions for computational efficiency. It will be understood to those of ordinary skill in the art, however, that each of the different tissues of the different regions may be assigned different standard characteristics or the characteristics may be extracted from images of the tissues, for example, from a CT scan.

Figure 5:
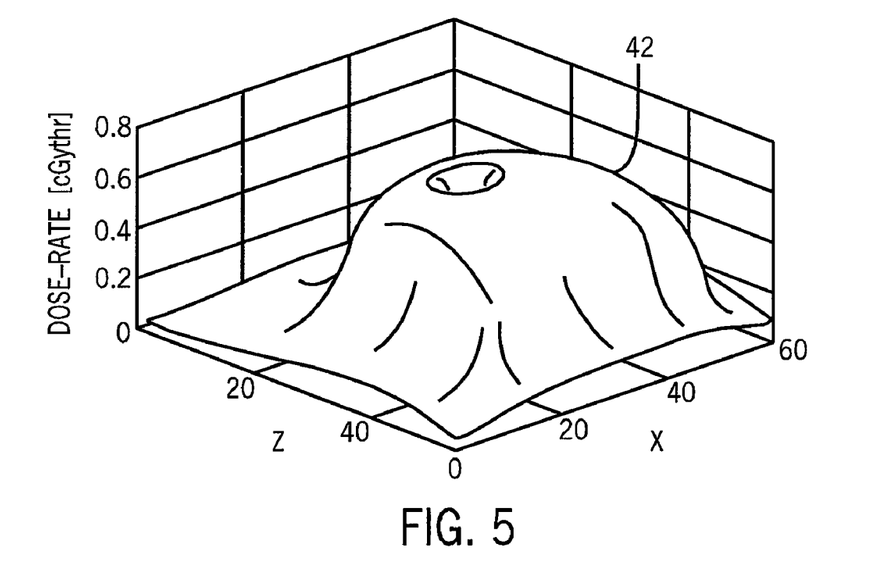
FIG. 5 is a perspective view of a three-dimensional plot of an adjoint function or importance function for a slice of the prostate showing an average dose received by the prostate as a function of location for a single source.

Referring now to FIG. 5, an adjoint function 42 for the prostate region 32 for an isotropic source (e.g. a source that emits radiation uniformly in all directions), intuitively shows that radioactive sources 12 placed within the outline of the prostate have the greatest effect on its average dose. In this depiction, the height of the surface represents an average dose and the plane over which the surface lies is an x-y plane of the image of the slice 30. Multiple planes are used to define the adjoint function in three dimensions.

Figure 6:
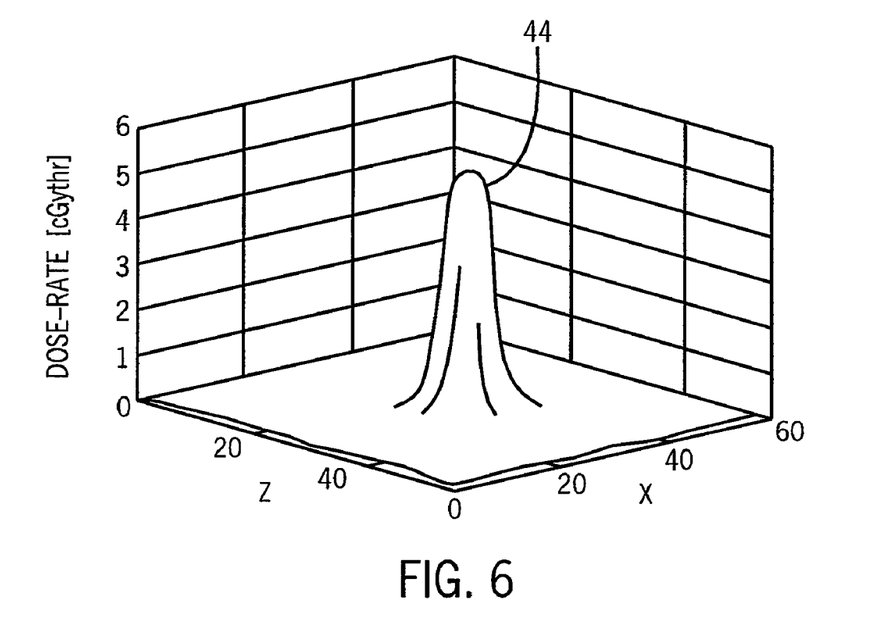
FIG. 6 is a figure similar to that of FIG. 5 showing an adjoint function or importance function for the urethra.
Figure 7:
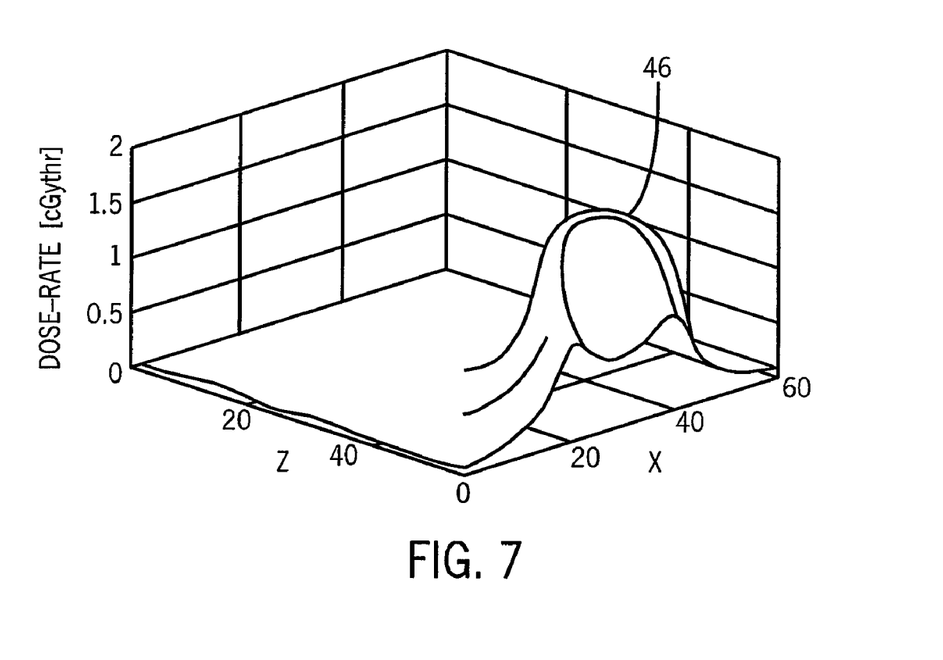
FIG. 7 is a figure similar to FIGS. 5 and 6 showing an adjoint function or importance function for the rectum.
Figure 8:
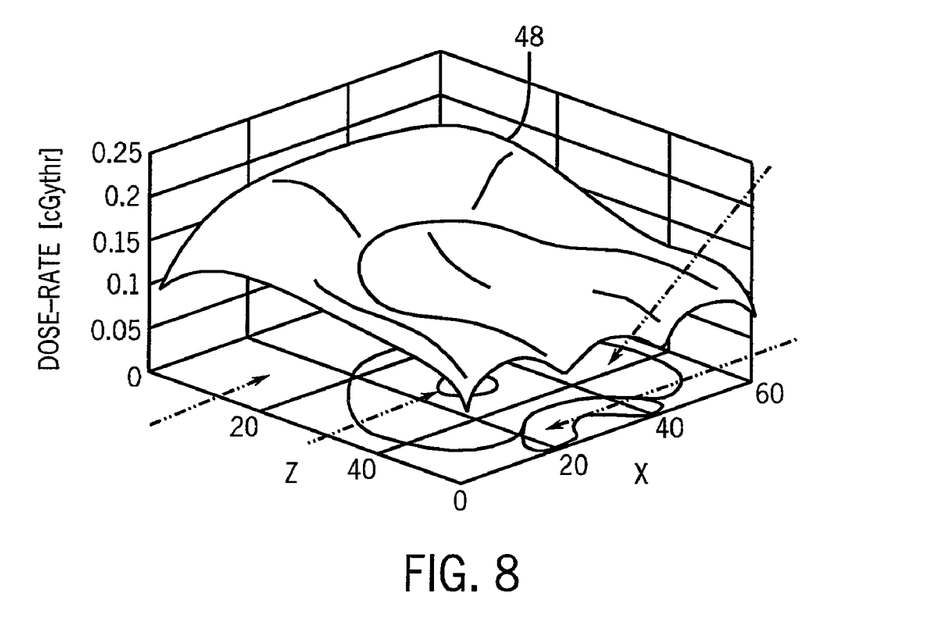
FIG. 8 is a figure similar to FIGS. 5 through 7 showing an adjoint function or importance function for margin tissue outside of the prostate.

Referring to FIG. 6 in a similar fashion, an adjoint function 44 for the urethra shows that isotropic radioactive sources 12 placed near the urethra provide the greatest average dose to the urethra. As shown in FIG. 7, a similar adjoint function 46 of the rectum may be determined, having peak values in the region of the rectum, and an adjoint function 44 of surrounding tissue (excluding the prostate, urethra, and rectum) may be determined, per FIG. 8, showing that source placement near the edges of the urethra or the prostate provide greatest average dose contribution to the respective surrounding tissue.

Figure 9:
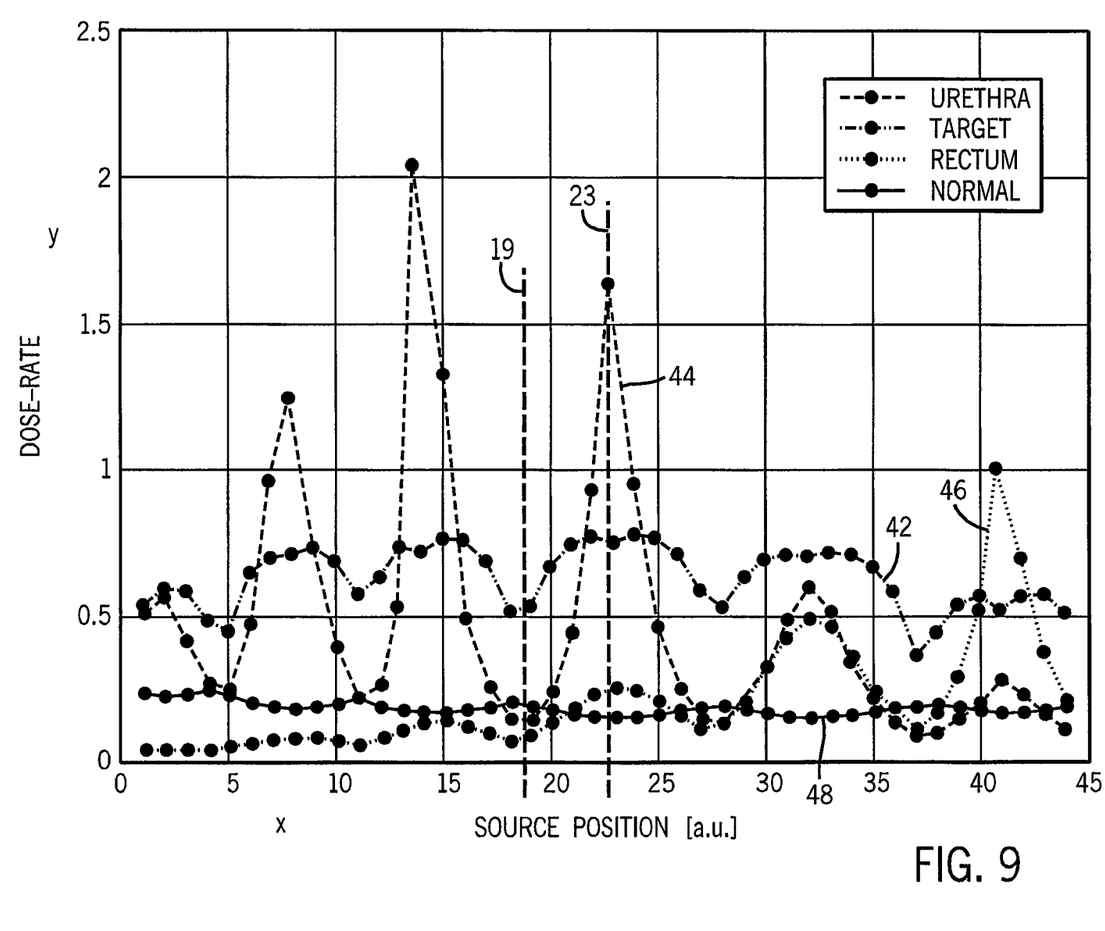
FIG. 9 is a two-dimensional plot of the adjoint functions of FIGS. 5 through 8, each reduced to a plot line by taking arguments along a raster pattern in the x-y plane of the corresponding ones of FIGS. 5 through 8 and showing two example locations producing high and low sensitivity for the urethra.

Referring now to FIG. 9, each of these three-dimensional surfaces of FIGS. 5 through 8 for the volume of the treatment area may be mapped to lines on a two-dimensional plot by following a raster pattern (or any systematic pattern) across the x-y plane of the adjoint functions of FIGS. 5 through 8 for multiple z planes. As shown in FIG. 9 at two particular locations 19 and 23, the adjoint functions of the various regions 32, 34, and 36 differ significantly. In this example, at location 23, being approximately centered within the image of the slice 30, the adjoint function 44 for the urethra is substantially higher in value than the value of the adjoint function 42 to the prostate, whereas at location 19, the adjoint function 42 of the prostate is much higher than that of the adjoint function 44 for the urethra. Intuitively, location 19 is a better location for a single source 12 than is location 23.

Figure 10:
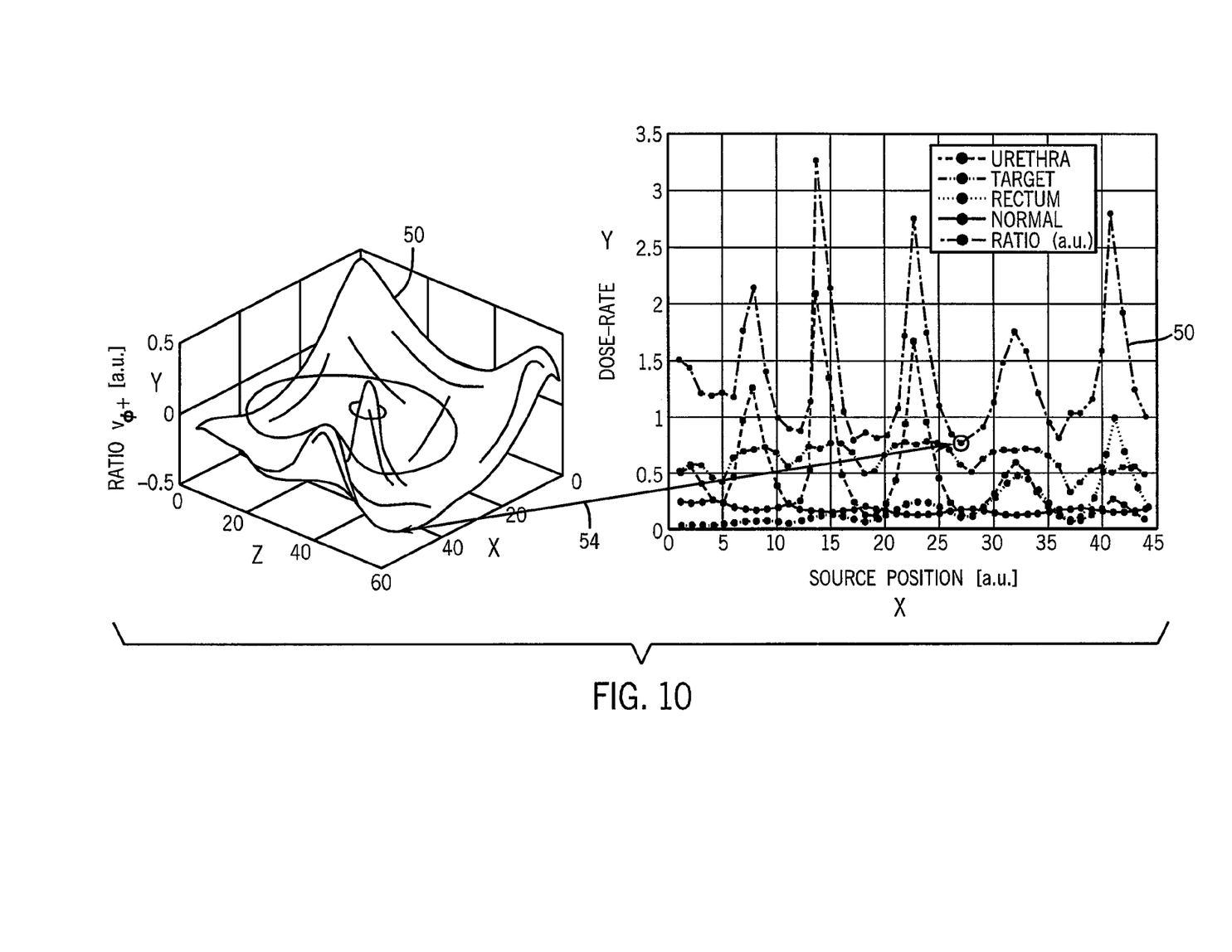
FIG. 10 is a three-dimensional and two-dimensional plot of an ex-ante importance function for a slice produced by taking a ratio of the sensitivities of the various structures and showing one example location producing high sensitivity of target and low sensitivity for the urethra, rectum and normal tissue.

Referring now to FIG. 10, this intuitive analysis may be quantified by calculating a ratio that provides an importance function 50, quantifying the relative sensitivities of the different regions according to the formula:

$$R(j) = \frac{w_{urethra} \cdot D^+_{j,urethra} + w_{rectum} \cdot D^+_{j,rectum} + w_{normal} \cdot D^+_{j,normal}}{D^+_{j,target}} \qquad (1)$$

where w is a weighting factor that indicates the relative importance of each region (being indicated by the subscript label: urethra, etc.) and D+ represents the value of the adjoint function 42 for the source at raster location j in each of the regions. An alternative formula could be $$R(j) = D^+_{j,target} - \sum_m w_m D^+_{j,m} \qquad (1a)$$

where m indicates a structure where dose should be held below a tolerance value.

As can be seen from inspection and reference to FIG. 9, this ratio will be small for values or locations where a radioactive source 12 will provide proportionally more radiation to the target than to non-target tissue and larger when the non-target tissue receives greater radiation.

For directional sources that preferentially emit radiation in certain directions, the above formula is modified by the addition of a source angle θ (typically within the slice 30 as discretized to given angle increments, for example 30°, at a location).

$$R(j, \theta) = \frac{w_{urethra} \cdot D^+_{j,\theta,urethra} + w_{rectum} \cdot D^+_{j,\theta,rectum} + w_{normal} \cdot D^+_{j,\theta,normal}}{D^+_{j,\theta,target}} \quad (2)$$

Here D+ represents the value of the adjoint function 42 for the source at raster location j and at angle θ in each of the regions. Copending provisional application entitled: "Directionally Emitting Radioactive Sources for Permanent Implantation" Ser. No. 11/130,967 filed May 17, 2004, assigned to the same assignee as the present invention, and hereby incorporated by reference, describes a method of creating sources 12 having a directional dose patterns.

This ratio may be plotted to a surface shown in FIG. 10 (shown for an isotropic source) for each z-plane, where low values indicate desirable locations for a single source 12 and form an ex ante importance function 50 used to guide source placement. The ex-ante importance function 50 differs from an "objective" function; the latter, which is usually used in iterative processes to determine how well a particular solution satisfies desired constraints. While the ex-ante importance function 50 provides an indication of desirable locations for a single source 12, because of its implicit averaging, it cannot show actual dose distribution, and thus cannot reveal the effectiveness of a set of sources 12 in producing a given dose distribution.

Referring again to FIG. 4, this calculation of the ex-ante importance function 50 is shown as process block 41 and, as indicated, may be pre-calculated because it does not change locally or incrementally during the treatment planning steps.

Determining Source Locations

Figure 11:
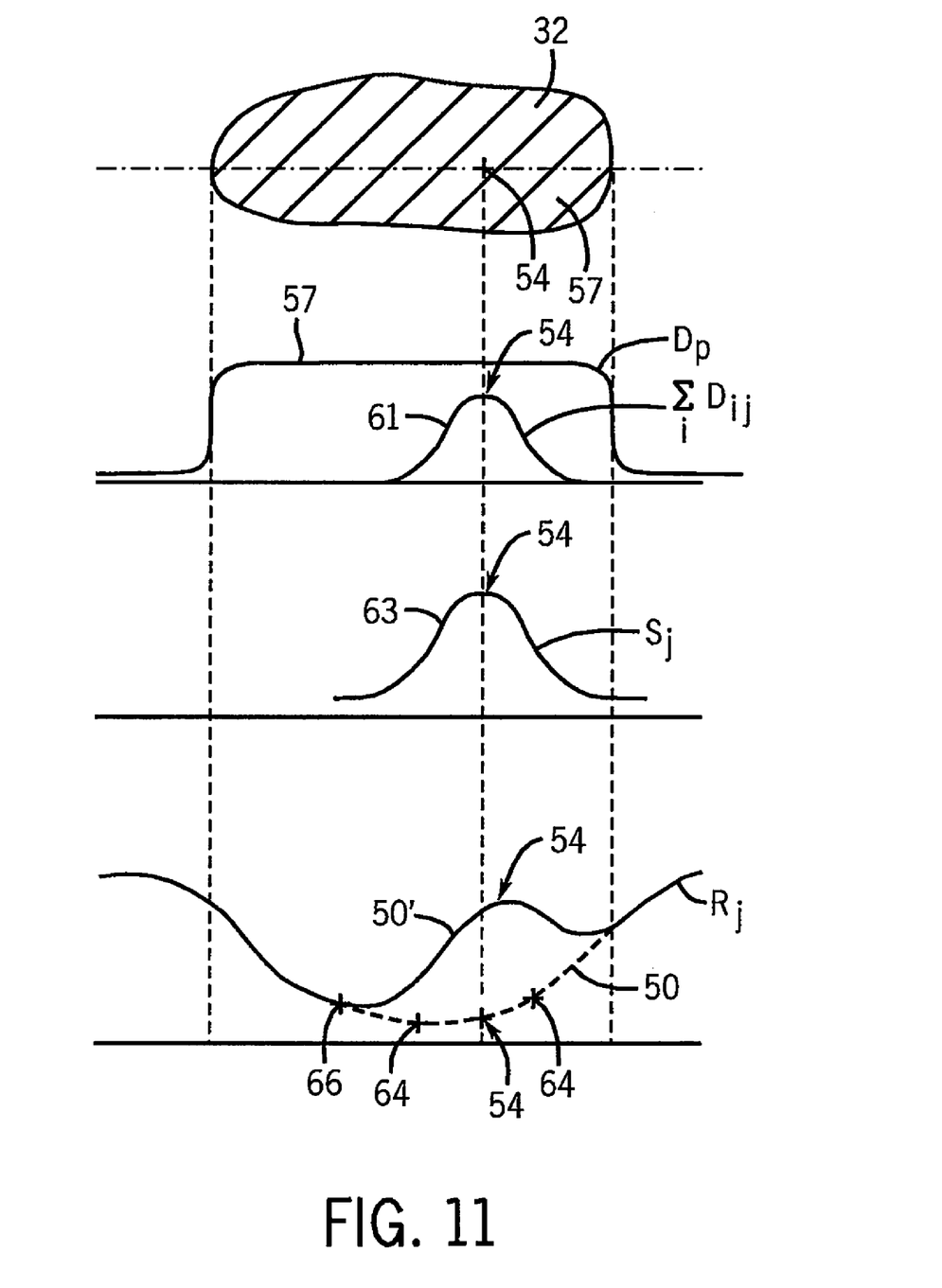
FIG. 11 is a set of four images, a reference plan region and three vertically aligned graphs; the uppermost being a plan view of the tumor region, the next being a graph of prescribed dose and total dose versus distance along an axis through the tumor indicated in the plan view, the next being a graph of a dose achievement function used to scale the importance function without requiring re-computation of the importance function, and the lowermost graph showing the effect of the dose achievement function on the importance function.

Referring now to FIGS. 4 and 11, at a next process block 51, each location j is ranked according to the value of the importance function 50 at that location j so that locations with the lowest value of the ratio of the importance function are given highest ranking. That is, the best source locations are ranked highest.

At process block 56, a location j for a new source is reserved based on that ranking, that is, by placing the source at the highest ranked location j not currently reserved for a source.

Referring to FIG. 11, an example source location 54 is shown positioned on a current dose pattern 61 in comparison with the prescribed dose pattern 57 selected in process block 28 and represents, initially, the lowest point in the surface of importance function 50 or the highest source in the ranking. Each subsequent source location j may be determined by taking the highest ranked location j not currently reserved, as will be described.

At next process block 58, shown in FIG. 4, this first source location 54 is used in computing a total dose from all the located sources thus far using standard forward dose modeling techniques. Initially, the total dose will be that of the source at location 54 alone; however, as source locations are reserved this will change. In this process, the contribution from a source at each reserved location need not be computed again but the additional dose provided by the last source simply added to the previous version of this calculation for time saving.

At decision block 59 shown in FIG. 4, the total dose provided by all of the located sources (sources at reserved locations), including at source location 54 as computed at process block 58, is evaluated against the prescribed dose 57 selected in process block 28, to see whether the dose is sufficient in coverage and/or uniformity over the prostate region 32 to conclude the treatment planning. In the preferred embodiment, this is done simply by evaluating the total area of the prostate region 32 where the dose exceeds a predefined limit (input at process block 28) and a predetermined percentage of the area of the prostate region 32 (also input at process block 28) and a variance limit within the prostate region 32 (also input at process block 28). If the sources provide a suitable treatment plan, that treatment plan is output as indicated by process block 78 and used for the guidance of placement of actual sources in the patient.

Accounting for Previously Reserved Source Locations

Assuming that the completion criterion has not yet been met, then at decision block 66, the program proceeds to process block 60 where a dose distribution function Sj 63 is determined over the whole target, reflecting generally the total dose (computed at process block 58) produced by the sources at the source locations that have been reserved so far as well as the most recent source placed at process block 56. This dose distribution function Sj 63 can then be applied to the importance function 50 to compute the evaluation function 50' without the need to recomputed importance function, thus greatly increasing the speed of this calculation. One possible dose achievement function Sj is provided below:

$$S_j = \frac{1}{Dp_j} \sum_{i=1}^{n} D_{ij} \quad (3)$$

where, Dpj is the original prescribed dose at location j (entered at process block 28) and Dij is the dose contributed to location j by all of the reserved sources over all locations i (calculated at process block 58).

Referring to FIG. 11, the prostate region 32, for example, may have an original prescribed dose Dp (57) within its boundaries, and these sources reserved so far may produce a total dose $$\sum_{i=1}^{n} D_{ij}, \quad (61)$$

for example produced by a single source at location 54. A resulting dose achievement function Sj (63) can then be computed having an increased value at location 54.

At process block 62, shown in FIG. 4, the importance function 50 computed at process block 41 is modified by multiplication of the importance function with the dose distribution function Sj on a point-by-point location as follows to give a new evaluation function, Ej:

$$E_j = R_j S_j \quad (4)$$

As shown in FIG. 11, this evaluation function will be used as a modified importance function 50' within a region around location 54, to replace the importance function as described below.

Referring still to FIG. 11, the effect of this modification (which does not require re-computation of the importance function 50) is that sources at locations 64 on the importance function 50 to the side of location 54, previously high in the ranking (per importance function 50), will be lowered (per importance function 50') in favor of sources that are farther away for example at location 66 farther from location 54.

This modified importance function 50' is then used to repeat the loop formed by process block 51, 56 and 58.

It will be understood that although the description above with respect to FIGS. 11 through 14 is shown on a two-dimensional slice, the actual planning is performed on a three-dimensional data set of multiple slices 30.

Evaluating Additional Treatment Options/Applications

Figure 15:
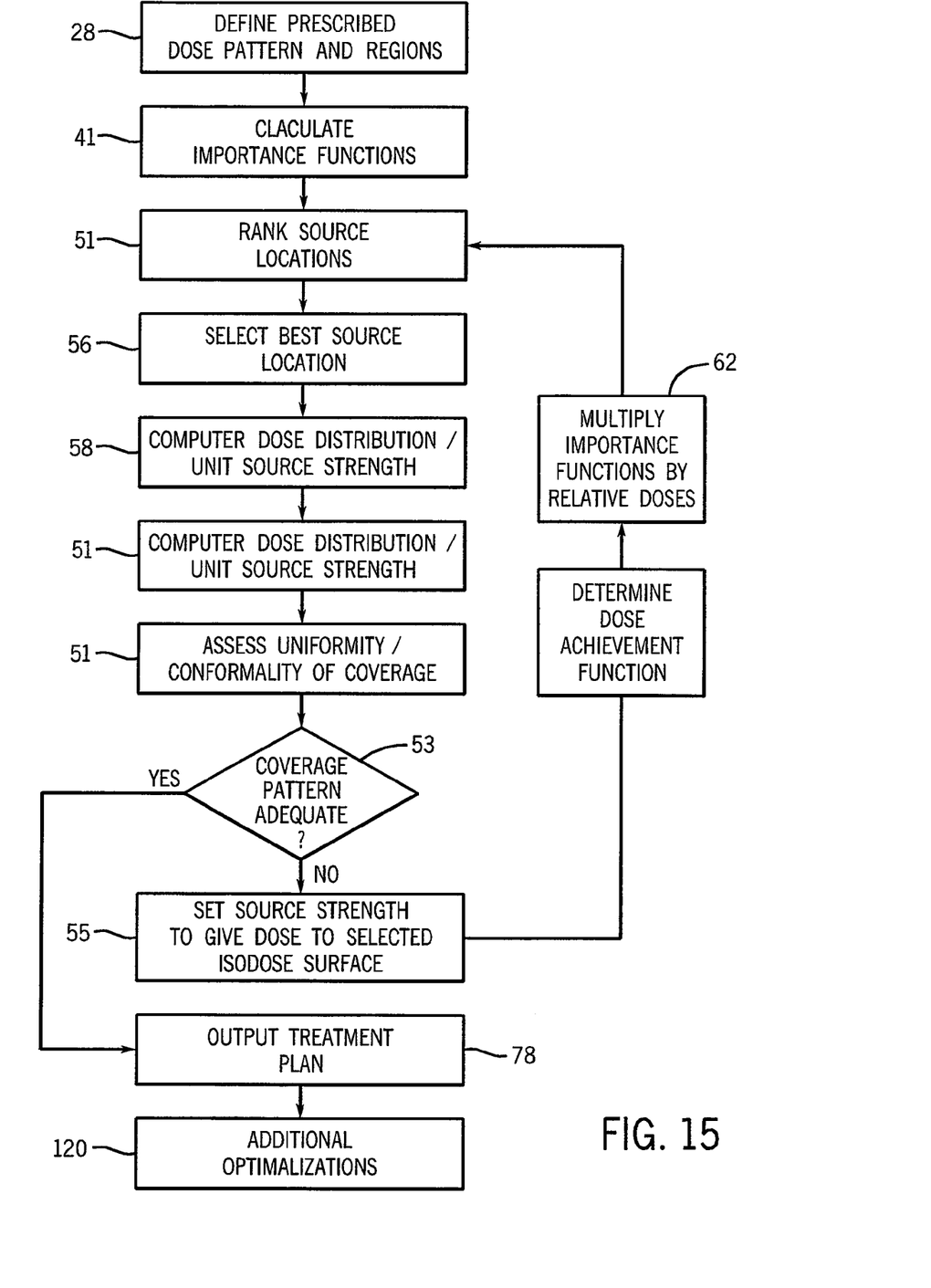
FIG. 15 is a figure similar to that of FIG. 4 showing an optimization technique providing an adjustment of source strength.

Referring now to FIG. 15, the rapid location of sources possible with the present invention makes it practical to repeat process blocks 51, 56, 58, 59, 60, and 62 multiple times with different options to optimize other parameters previously set at process block 28. For different applications process block 41 can be computed differently for example, the total number of sources 12, the orientation of directional sources, a mix of different strengths of sources 12, and the placement of sources at on/off-grid locations 20 may be varied and multiple importance functions can be computed at process block 41. A ranking may be jointly developed from these multiple importance functions (which in themselves constitute an importance function) so as to develop a radiation therapy treatment plan output at process block 78 that may indicate not only the locations 54 of the sources 12 but the type of sources, source orientation, and the particular needles associated with each source.

Figure 12:
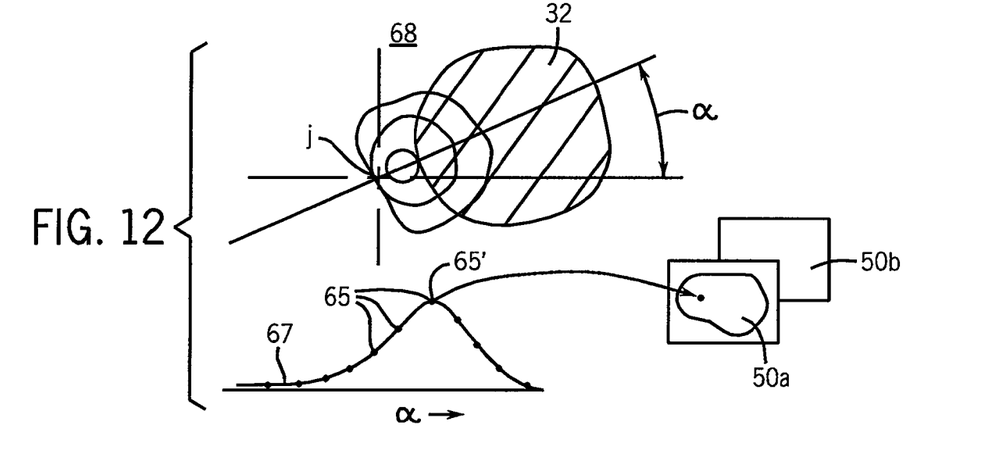
FIG. 12 is a plan view of a directional source at a given position and angular orientation with respect to a tumor, the plan view position above a graph showing the value of the importance function at the given position for different orientations of the source, showing a mapping of selected preferred orientation to a point on a different importance function.

Referring now to FIG. 12, by way of example, the accommodation of directional sources may be provided by simply computing multiple adjoint functions for each given location j with the virtual source in different rotational orientations α to provide a adjoint function distribution 67. Thus as shown in FIG. 12, at a given location j, a virtual source is rotated through multiple discrete angles α (for example every 30°) and the dose pattern 68 at that particular angle α used to compute an adjoint function value 65 associated with the rotational angle α. The best adjoint function value 65' of the adjoint function distribution 67 is then used to generate one data point for an importance function 50a for directional sources. In one embodiment, this importance function 50a is then used at process block 41 described above.

When a mixed treatment of directional and isotropic sources is required, a separate importance function 50b may be created for isotropic sources. The ranking at process block 51 of FIG. 4 then simply selects for each location j the better (lower) value among the importance functions 50a and 50b for that point j.

It has been determined that this straightforward approach to generating a treatment plan using mixed directional and isotropic sources tends to favor directional sources over isotropic sources. This bias can be corrected in two ways. The first way simply decreases the weights associated with the numerator of the importance functions 50b corresponding to the isotropic seeds shown in equations (1) and (2). Directional sources tend to favor differentiation between tumor and non-tumor tissue, this de-weighting increases the advantage of isotropic sources favoring their selection. The weighting may be adjusted until a desired ratio of directional and isotropic sources is generated, for example 50%.

An alternative approach evaluates the variance in the adjoint function distribution 67 (shown in FIG. 12) relating angle α of the directional sources to its adjoint function value 65. This variance quantifies the potential advantage of the directional source at any location j. If the variance is high, the directional source provides substantial benefit over an isotropic source and is favored; when the variance is low the directional source provides little advantage over an isotropic sources and is disfavored. This variance may be incorporated into the process of selecting among importance functions 50a and 50b by using a variance threshold on variance of values of importance functions 50a of the directional source. If the variance is above that threshold selecting a directional source, and if it is below that threshold accepting an isotropic source. Another alternative is to use the difference approach as in equation (1a). This will favor isotropic sources at locations centered in the target or far from structures to avoid.

Figure 13:
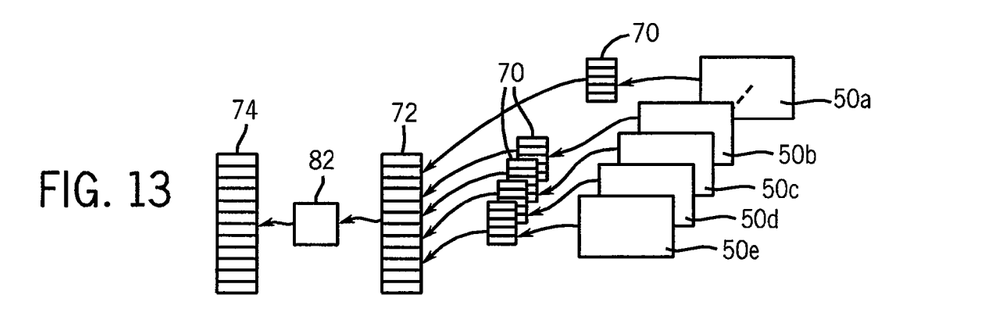
FIG. 13 is a data flow diagram showing the determination of rankings from each importance function that are collected into a common ranking and then weighted by a needle function to reduce an ultimate ranking.

Referring now to FIG. 13, this general approach may be used to evaluate a wide variety of treatment plan options, for example, selecting among sources of different types (e.g. radionuclides), different directionality, different strength etc. Each of these different options can be represented by a different importance function 50a-50e, each importance function 50 with its own ranking 70 representing the best location of a source for a particular isotope, direction, strength, etc. These rankings 70 may be combined to produce a master ranking 72 that may be used in the present invention allowing the ultimate treatment plans to consider and select among all of these options.

The master ranking 72 may be further modified, for example, to impose constraints on the treatment plan. A particular constraint of interest is represented by ranking modifier 82 that serves to limit the number of needles or needle tracks required at every step in a given treatment plan under construction. This may be done by the use of a needle penalty function 75 that modifies the master ranking 72 to produce a modified ranking 74.

Figure 14:
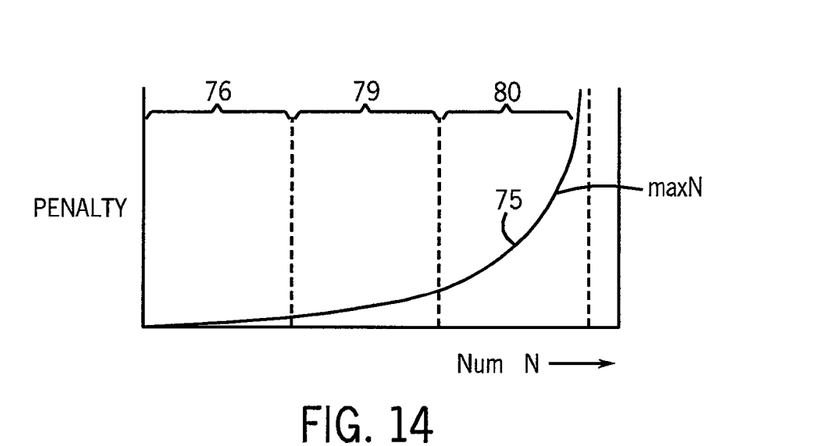
FIG. 14 is a graphical representation of a typical needle penalty function.

Referring to FIG. 14, ideally, the needle penalty function 75 is a function of the number of needles (NumN) needed for the addition of a given source and thus is determined during the source placement process, and a user-specified maximum number of needles (maxN). The needle penalty function 75 will include a threshold region 76, a slow growth region 79, and a fast growth region 80, with the needle penalty function 75 rising rapidly at the maximum number of needles (maxN). An example of many possible penalty functions is as follows:

$$\text{Penalty}(NumN) = \frac{1}{2} \left[ \frac{\max N^2 + (NumN + 1)^2}{\max N^2 - (NumN + 1)^2} \right]^{1/2} \quad (5)$$

The penalty function will thus generally enforce a limit to the number of needles in the fast growth region 80 but will be largely indifferent to the number of needles for small needle numbers in the threshold region 76 and the slow growth region 79 preferring instead optimal source placement. Through use of the needle penalty function 75, additional treatment preferences may be enforced.

The needle penalty function may be applied by multiplying the importance function values enrolled in the master ranking 72 by the needle penalty function 75, accepting as an argument a number of needles used by all previously reserved sources and the current source under consideration. Thus, if the current location of the master ranking does not require a new needle, the previous number of needles is used without needle penalty; however, if the new source location requires a new needle, the previous number of needles plus one is used to calculate the penalty. The penalty function is applied by multiplying the importance function values with penalty. This produces a new ranking 74, which is then used in the process described with respect to FIG. 4.

Incorporation of Dose Homogeneity for Additional Applications

Improved homogeneity in the dose, for example, may be obtained by modifying the importance function to incorporate this measure, for example a new evaluation function may be as follows:

$$E_j = DNR_j * S_j * S_{DNR,j} \quad (6)$$

where DNRj is any convenient homogeneity measurement, for example hot-spots within the target prostate region 32 that can be pre-computed as importance function at process block 41 assessing dose homogeneity contribution of a hypothetical source at a location j for a variable amount of time, or:

$$DNR_{j \in target} = \frac{V150}{V100} \quad (7)$$

where V100 is the percentage of the target volume 32 irradiated to doses equal to or greater than 100% of the prescribed dose 57 and V150 is the percentage of the target volume 32 irradiated to doses equal to or greater than 150% of the prescribed dose 57. Referring to FIG. 15, SDNR,j is the dose homogeneity function, akin to dose distribution function Sj, it computes the dose homogeneity of the treatment plan from all the sources at the reserved locations. For application of dwell time optimization in high dose rate implants, the new evaluation function Ej can be used to find out maximum allowed time for which the source may be placed at location j by repeated selection of source reservation at location j before Ej degrades at that location j, and then location j is reserved for a given dwell time as a multiple of 0.1 s (or any minimum time increment) and hypothetical source is moved to next top-ranked location following rankings corresponding to the last value of the evaluation function Ej.

Other indicators for homogeneity, such as the conformality index, $$ConformalityIndex = \frac{V100}{VolumeOf100\%} \cdot \frac{V100}{TargetVolume}$$

could also be used for seed strength optimization as follows.

Referring now to FIG. 15, when different source strengths are available, they may be selected among and optimized by using the same process described with respect to FIG. 4 but with decision block 59 being replaced by process block 51, decision block 53, and process block 55. Process box 51 assesses the current dose produced by the reserved source locations but strictly according to the criterion of conformity or uniformity of coverage.

At succeeding decision block 53, coverage pattern is assessed considering not only the uniformity and conformity of the coverage but the absolute dose levels. If both uniformity or conformity and dose level are satisfied, a treatment plan may be output per process box 78. If not, however, the program proceeds to process block 55 and the strength of the sources is adjusted to produce the desired dose level. A dose distribution function is then determined at process block 60 and the importance function weighted per process block 62 as before.

The speed advantages provided by the present invention make real-time treatment planning possible in which the patient is positioned, for example, on a treatment table and scanned in a CT machine or the like, and then, while maintaining registration with the scanning table, is treated using a treatment plan developed from the present invention without repositioning of the patient. In this case, the grid plate 16 of FIG. 1 may be attached to the scanning table. In addition the high-speed operation of the present invention allows the treatment plan to be modified based on actual placement of the sources.

It is specifically intended that the present invention not be limited to the embodiments and illustrations contained herein, but include modified forms of those embodiments including portions of the embodiments and combinations of elements of different embodiments as come within the scope of the following claims.

We claim:

1. A method of treatment planning for placement of radioactive sources in a tumor in a region of a body comprising the following steps, in the indicated order, of:
   (a) determining an original prescribed dose for a range of locations within the region of the body;
   (b) calculating an importance function for the range of locations based on a dose produced by a hypothetical source moved among the range of locations;
   (c) ranking the range of locations according to the importance function;
   (d) based on the ranking, identifying a source location not currently reserved for a source and reserving that identified location;
   (e) creating an evaluation function being a modification of the importance function according to a dose distribution function based on total dose provided by sources reserved at locations;
   (f) repeating steps (c)-(e) using the evaluation function in lieu of the importance function for steps (c)-(d) until the dose provided by sources at reserved locations matches the original desired dose pattern to within a predetermined matching criterion; and
   (g) irradiating the region of the body with at least one radioactive source located at each of the reserved locations;
   wherein calculating the evaluation function increases the importance function by a function related to the total dose provided by hypothetical sources at currently reserved locations and the prescribed dose.

2. The method of claim 1 wherein calculating the evaluation function scales values of the importance function by a function related to a ratio of the total dose provided by hypothetical sources at currently reserved locations and the prescribed dose.

3. The method of claim 1 wherein the treatment plan describes a positioning of sources implanted at each of the reserved locations.

4. The method of claim 1 wherein the treatment plan describes movement of a movable radioactive source among the reserved locations.

5. The method of claim 1 wherein the importance function is a ratio of amount of dose to the tumor tissue versus an amount of dose to non-tumor tissue.

6. The method of claim 1 wherein the importance function incorporates homogeneity of the dose in the tissue being treated.

7. The method of claim 1 wherein the matching criterion is selected from the group consisting of uniformity and conformity and including the step of selecting source strength after the matching criterion is met to produce the desired dose distribution.

8. The method of claim 1 wherein the range of locations is not limited to regular grid locations.

9. The method of claim 1 wherein the ranking orders source locations according to the evaluation function as modified by a needle function, the needle function accepting as an argument a total number of needles necessary to locate sources at currently reserved locations and a given location in the ranking, the needle function decreasing a weight of the importance function for the given location in the ranking as the number of needles increases.

10. The method of claim 9 wherein the needle function rises sharply approaching a pre-defined maximum number of needles.

11. The method of claim 1 wherein the importance function considers a hypothetical directional source at different rotated orientations and the ranking adopts a rotation having a best value of the importance function among the directional source at the different rotated orientations.

12. The method of claim 11 wherein the importance function considers both hypothetical directional sources and hypothetical isotropic sources and the ranking adopts an isotropic source when a variance of importance functions values, for a directional source at the same location and different rotations, is below a predetermined threshold.

13. The method of claim 11 wherein the importance function evaluates an amount of dose to the tumor tissue versus an amount of dose to a non-tumor tissue; and
wherein the importance function considers both hypothetical directional sources and hypothetical isotropic sources and the importance function for hypothetical isotropic sources provides lower weighting to the non-tumor tissue dose so that most sources selected in the ranking are isotropic.

14. The method of claim 1 wherein the importance function considers different species of hypothetical sources and the ranking adopts the species having a best value of importance function for a given location among the different species.

15. Treatment planning software for placement of radioactive sources in a tumor in a region of a body, the treatment planning software fixed in tangible medium for execution on electronic computer to:
(a) accept a prescribed dose pattern for a range of locations within the region of the body;
(b) calculate an importance function for the range of locations based on dose provided to the regions of the body by a hypothetical source moved among the range of locations;
(c) rank the range of locations according to the importance function;
(d) based on the ranking, identify a source location not currently reserved for a source and reserving that identified location;
(e) generate an evaluation function being a modification of the importance function according to a dose distribution function based on total dose provided by sources reserved at locations;
(f) repeat steps (c)-(e) using the evaluation function in lieu of the importance function for steps (c)-(d) until the total dose provided by sources at reserved locations matches the prescribed dose pattern to within a predetermined matching criterion; and
(g) output to a user a treatment plan to be used for treating a patient by irradiating the region of the body with at least one radioactive source located at each of the reserved locations;
wherein calculating the evaluation function increases the importance function by a function related to the total dose provided by hypothetical sources at currently reserved locations and the prescribed dose.

16. The treatment planning software of claim 15 wherein the calculation of the evaluation function scales values of the importance function by a function related to the total dose provided by hypothetical sources at currently reserved locations.

17. The treatment planning software of claim 16 wherein the calculation of the evaluation function gets re-computed as a ratio of the prescribed dose and the total dose provided by hypothetical sources at currently reserved locations.

18. The treatment planning software of claim 15 wherein the evaluation function measures homogeneity of the dose to tissue being treated.

19. The treatment planning software of claim 15 wherein the ranking orders source locations according to the evaluation function as modified by a needle function, the needle function accepting as an argument a total number of needles necessary to locate sources at currently reserved locations and a given location in the ranking, the needle function decreasing a value of the evaluation function for the given location in the ranking as the number of needles increases.

20. The treatment planning software of claim 15 wherein multiple importance functions are calculated for different treatment options to produce multiple rankings that may be combined to choose a best treatment option, wherein the importance functions may relate to a least one of the treatment options selected from the group consisting of: directional sources at different rotational orientations, mixtures between sources with different radioisotopes, mixtures between isotropic and anisotropic sources, source locations at non-template positions, locations of temporary sources and locations of a single source for variable dwell times at different locations.

21. An electronic computer executing a method of treatment planning for placement of radioactive sources in a tumor in a region of a body comprising the following steps, in the indicated order, of:
(a) determining an original prescribed dose for a range of locations within the region of the body;
(b) calculating an importance function for the range of locations based on a dose produced by a hypothetical source moved among the range of locations;
(c) ranking the range of locations according to the importance function;
(d) based on the ranking, identifying a source location not currently reserved for a source and reserving that identified location;
(e) creating an evaluation function being a modification of the importance function according to a dose distribution function based on total dose provided by sources reserved at locations;
(f) repeating steps (c)-(e) using the evaluation function in lieu of the importance function for steps (c)-(d) until the dose provided by sources at reserved locations matches the original desired dose pattern to within a predetermined matching criterion; and
(g) outputting a treatment plan to be used for treating a patient by irradiating the region of the body with at least one radioactive source located at each of the reserved locations;
wherein calculating the evaluation function increases the importance function by a function related to the total dose provided by hypothetical sources at currently reserved locations and the prescribed dose.

* * * * *